United States Patent
Docherty et al.

(10) Patent No.: US 11,551,790 B2
(45) Date of Patent: Jan. 10, 2023

(54) SYSTEMS, DEVICES, AND METHODS FOR INGESTIBLE EVENT SENSING AND ANALYSIS

(71) Applicant: OTSUKA PHARMACEUTICAL CO., LTD., Tokyo (JP)

(72) Inventors: John P. Docherty, New York, NY (US); Ainslie Hatch, Princeton, NJ (US); Ruth Ross, Independence, VA (US); Dawn I. Velligan, San Antonio, TX (US); Peter Weiden, Newton, MA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 875 days.

(21) Appl. No.: 15/673,870

(22) Filed: Aug. 10, 2017

(65) Prior Publication Data
US 2017/0337330 A1 Nov. 23, 2017

Related U.S. Application Data

(63) Continuation of application No. PCT/JP2016/000708, filed on Feb. 10, 2016.
(Continued)

(51) Int. Cl.
*G16H 10/60* (2018.01)
*G16H 40/63* (2018.01)
(Continued)

(52) U.S. Cl.
CPC ............ *G16H 10/60* (2018.01); *G16H 20/10* (2018.01); *G16H 20/60* (2018.01); *G16H 40/63* (2018.01); *G16H 40/67* (2018.01)

(58) Field of Classification Search
CPC ..................................................... G16H 20/10
See application file for complete search history.

(56) References Cited

U.S. PATENT DOCUMENTS 10,521,561 B1 * 12/2019 Euliano .................. G16H 40/67
2008/0020037 A1    1/2008 Robertson et al.
(Continued)

FOREIGN PATENT DOCUMENTS

| CN | 101686800 A | 3/2010 |
| CN | 203342049 U | 12/2013 |

(Continued)

OTHER PUBLICATIONS

Office Action for European Application No. 16748931.9, dated Apr. 3, 2020, 6 pages.
(Continued)

*Primary Examiner* — Robert A Sorey
*Assistant Examiner* — Kristine K Rapillo
(74) *Attorney, Agent, or Firm* — Cooley LLP

(57) ABSTRACT

In some embodiments, a system includes an ingestible signal generator coupled to a medication and configured to generate a body-transmissible signal upon ingestion by a user. The system also includes a receiver, the receiver including a sensor configured to detect the body-transmissible signal, the receiver configured to generate and wirelessly transmit a sensor signal based on the body-transmissible signal. The system also includes a user device. A processor of the user device is configured to wirelessly monitor the sensor for the sensor signal and, in response to not receiving the sensor signal within a predetermined time period, generate a notification. The processor is further configured to send a signal to present the notification and receive a response to the notification from the user. The processor is also configured
(Continued)

to identify at least one trend associated with the sensor signal and the medication, and perform an action based thereon.

27 Claims, 9 Drawing Sheets

Related U.S. Application Data

(60) Provisional application No. 62/114,787, filed on Feb. 11, 2015.

(51) Int. Cl.
*G16H 20/10* (2018.01)
*G16H 20/60* (2018.01)
*G16H 40/67* (2018.01)

(56) References Cited

U.S. PATENT DOCUMENTS

| | | | |
|---|---|---|---|
| 2010/0241454 A1 | 9/2010 | Firminger et al. | |
| 2012/0173319 A1 | 7/2012 | Ferrara | |
| 2013/0096953 A1* | 4/2013 | Beverly | G16H 40/67 705/3 |
| 2013/0117696 A1 | 5/2013 | Robertson et al. | |
| 2014/0309505 A1 | 10/2014 | Euliano et al. | |
| 2015/0100335 A1* | 4/2015 | Englehard | G16H 40/63 705/2 |
| 2015/0100343 A1* | 4/2015 | Siedlecki | G16H 20/10 705/2 |
| 2015/0127380 A1* | 5/2015 | Aaron | G16H 10/60 705/3 |
| 2016/0132660 A1 | 5/2016 | Barajas et al. | |

FOREIGN PATENT DOCUMENTS

| | | |
|---|---|---|
| TW | M491911 U | 12/2014 |
| WO | WO 2006/116718 | 11/2006 |
| WO | WO 2008/008281 | 1/2008 |
| WO | WO 2008/063626 | 5/2008 |
| WO | WO 2008/095183 A2 | 8/2008 |
| WO | WO 2014/004437 | 1/2014 |
| WO | WO-2014197774 A2 | 12/2014 |
| WO | WO-2016129286 A1 | 8/2016 |

OTHER PUBLICATIONS

Extended European Search Report for European Application No. 16748931.9, dated Jul. 31, 2018, 10 pages.

Hafezi, H. et al., "An ingestible sensor for measuring medication adherence," IEEE Transactions on Biomedical Engineering, vol. 62, No. 1, Jan. 2015, pp. 99-109.

Kane, J. M. et al., "Non-adherence to medication in patients with psychotic disorders: epidemiology, contributing factors and management strategies," World Psychiatry, vol. 12, No. 3, Oct. 2013, pp. 216-226.

International Search Report for International Application No. PCT/JP2016/000708, dated Apr. 5, 2016, 5 pages.

Otsuka Pharmaceutical Co., Ltd., "U.S. FDA Accepts First Digital Medicine New Drug Application for Otsuka and Proteus Digital Health," [online] Sep. 11, 2015 [Retrieved on Mar. 25, 2016], Retrieved from the Internet: <URL: http://www.otsuka.co.jp/en/comp>, 2 pages.

Toda, T. et al., "Development of Interactive Communication System for Supporting Outpatient Medical Treatment with Considering User Experience," Journal of Human Interface Society, Aug. 25, 2010, vol. 12, No. 3, pp. 11-20 (with English Abstract).

International Preliminary Report on Patentability for International Application No. PCT/JP2016/000708, dated Aug. 15, 2017, 6 pages.

Office Action dated Aug. 3, 2020, issued in the corresponding Chinese Patent Application No. 201680009399.7.

Office Action for Australian Application No. 2016217324 dated Mar. 9, 2021, 9 pages.

Examination Report No. 1 for Australian Application No. 2016217324, dated Nov. 18, 2020, 6 pages.

\* cited by examiner

SYSTEMS, DEVICES, AND METHODS FOR INGESTIBLE EVENT SENSING AND ANALYSIS

CROSS REFERENCE TO RELATED APPLICATIONS

This application is a continuation of PCT Application No. PCT/JP2016/000708 titled "SYSTEMS, DEVICES, AND METHODS FOR INGESTIBLE EVENT SENSING AND ANALYSIS", filed Feb. 10, 2016, which claims priority to U.S. Provisional Application No. 62/114,787 titled "SYSTEMS, DEVICES, AND METHODS FOR ASSESSING NON-ADHERENCE TO A MEDICATION REGIMEN", filed Feb. 11, 2015, the entire disclosures of which are incorporated herein by reference in their entireties.

BACKGROUND

Some known methods to measure medication adherence, including patient self-reports, pill counts, refill rates, biological monitoring, and electronic monitoring, are proxy measures. As an example, patient self-reports rely on memory and can be prone to inaccuracies and recall bias. Pill counts can be unreliable if patients fail to return bottles and/or discard pills before the count. As another example, biological monitoring (e.g., sampling blood, urine) can be impractical, invasive, and/or intrusive and usually cannot measure adherence unless the time and dose administered before sampling are verified. As yet another example, refill rates or electronic monitoring are often indeterminate on whether patients actually took a medication.

Thus, there exists a need for systems, devices and methods that can more accurately sense ingestion-related events, and analyze the events for potentially triggering one or more actions, such as, for example, directed to assuring patient compliance.

SUMMARY

In some embodiments, a system includes an ingestible signal generator coupled to a medication and configured to generate a body-transmissible signal upon ingestion by a user. The system also includes a receiver including a sensor configured to detect the body-transmissible signal. The receiver is configured to generate and wirelessly transmit a sensor signal based on the body-transmissible signal. The system also includes a user device. A processor of the user device is configured to wirelessly monitor the sensor for the sensor signal and, in response to not receiving the sensor signal within a predetermined time period, generate a notification. The processor is further configured to send a signal to present the notification to the user and receive a response to the notification from the user. The processor is also configured to identify at least one trend associated with the sensor signal and the medication. The processor is also configured to perform one or more actions based on the response and the at least one trend.

BRIEF DESCRIPTION OF THE DRAWINGS

FIGS. 5A-5E are screenshots of an exemplary interface for assessing non-adherence, according to an embodiment.

FIG. 7 is a screenshot of an exemplary interface for viewing data associated with patient adherence/non-adherence to a medication regimen, according to an embodiment.

DETAILED DESCRIPTION

Figure 1:
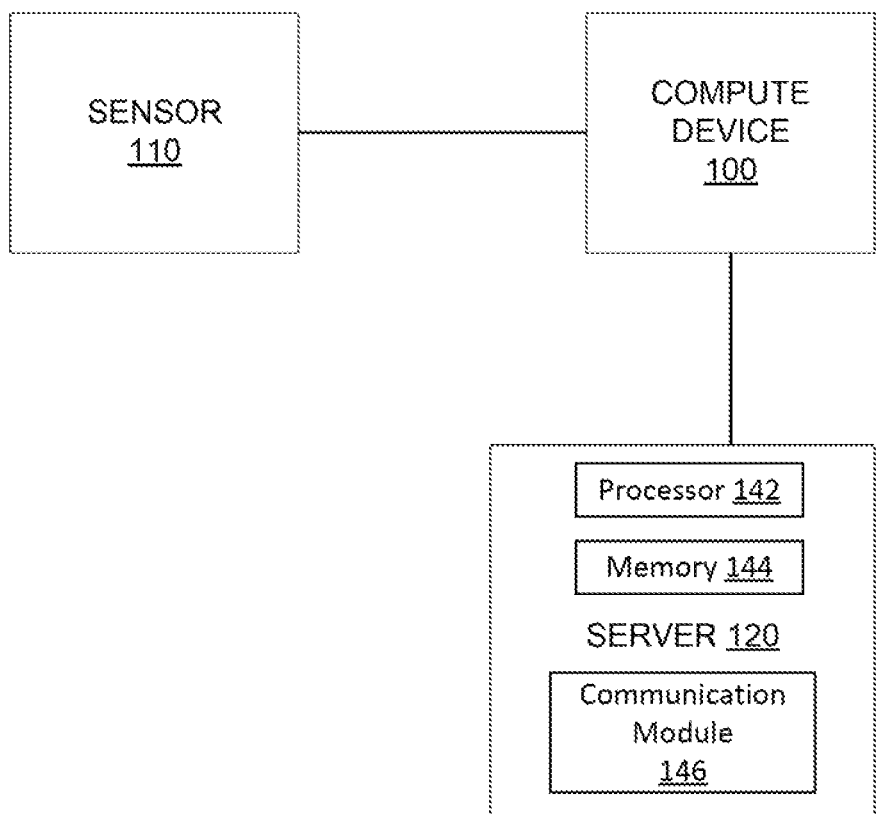
FIG. 1 is an illustration of a system for event sensing and analysis, according to an embodiment.

Systems, devices and methods are described herein for ingestible event sensing and analysis, such as for assessing compliance and/or noncompliance (also referred to as adherence and/or non-adherence) to a medication regimen based on detection of ingestion of a substance (e.g., a medication). In some embodiments, a system includes an ingestible signal generator coupled to a medication and configured to generate a body-transmissible signal upon ingestion by a user. The system also includes a receiver including a sensor configured to detect the body-transmissible signal. The receiver is configured to generate and wirelessly transmit a sensor signal based on the body-transmissible signal. The system also includes a user device. A processor of the user device is configured to wirelessly monitor the sensor for the sensor signal and, in response to not receiving the sensor signal within a predetermined time period, generate a notification. The processor is further configured to send a signal to present the notification to the user and receive a response to the notification from the user. The processor is also configured to identify at least one trend associated with the sensor signal and the medication. The processor is also configured to perform one or more actions based on the response and the at least one trend.

Embodiments described herein enable, via ingestion sensing and analysis, monitoring of patient noncompliance based on the lack of detection of an ingestion event, and dynamic determination of the reason(s) for noncompliance. Embodiments described herein also enable various entities involved in patient health management, such as caregivers, prescribers, and/or the patient, to actively learn of a single occurrence and/or recurring occurrences of noncompliance, thereby mitigating therapeutic risk associated therewith.

The substance can encompass any suitable ingestible component such as, but not limited to, medication (including pharmaceutical excipients), food, supplements (e.g., vitamins or protein), biological agents (e.g., oral vaccines), ingestion tracking agents (e.g., ingestible event markets/identifier) and combinations thereof. The substance can be in substantially solid form, in substantially liquid form, or any suitable state in-between that is ingestible. The ingestible component can encompass both digestible and indigestible components. In some embodiments, the substance includes at least one ingestion tracking agent, and at least one other component.

Aspects of the systems, devices, and methods described herein are further operable to identify trends in adherence of the user with the therapeutic regimen based on the monitoring of ingestion of the substance. In some embodiments, for example, an apparatus includes a sensor module configured to monitor a sensor for a sensor signal indicative of ingestion of a substance by a user. The apparatus can further include an adherence module configured to, in response to the sensor module not receiving an indication within a predetermined time period that the sensor received the sensor signal, generate a query indicative of noncompliance of the user with a therapeutic regimen associated with the substance. The query solicits a set of responses. The apparatus can further include a communication module configured to transmit the query to the user, and receive, in response to the query, an indication of a selection of a response from the set of responses. The apparatus can further include an analytics module configured to identify at least one trend associated with compliance of the user with the therapeutic regimen based on at least one of the response from the set of responses, timing information associated with the response from the set of responses, timing information associated with historical data of compliance of the user with the therapeutic regimen, frequency information associated with the response from the set of responses, or frequency information associated with historical data of compliance of the user with the therapeutic regimen.

In some embodiments, the set of responses is a first set of responses. In some embodiments, the adherence module is configured to, in response to receiving the selection of the response from the first set of responses from the communication module, remove the response from the first set of responses to define a modified first set of responses and generate a modified query including the modified first set of responses. In some embodiments, the communication module is configured to transmit the modified query to the user, and receive a selection of a response from the modified first set of responses different from the response from the first set of responses. In some embodiments, the communication module is further configured to, when the response from the modified first set of responses indicates user intent to provide additional user input, transmit to the user a second set of responses associated with the response from the modified first set of responses.

In some embodiments, the apparatus further includes an action module. In some embodiments, the action module is configured to perform one or more actions based on the response from the set of responses. In some embodiments, the action module is configured to identify a remedial communication associated with the response from the set of responses, and the communication module configured to transmit the remedial communication to the user. In some embodiments, the communication module is configured to transmit information associated with the response from the set of responses to at least one of the user, a caregiver of the user, a healthcare provider of the user, or an entity associated with the substance.

In some embodiments, the apparatus further includes a database module. In some embodiments, the database module is configured to store in a database the response from the set of responses.

In some embodiments, the predetermined time period is a first predetermined time period, and the adherence module is configured to generate an indication associated with detection of ingestion of the substance during a second predetermined time period. In some embodiments, the database module is configured to store in a database the response from the set of responses and the indication. In some embodiments, the analytics module is configured to retrieve the response from the set of responses and the indication from the database prior to the analytics module identifying at least one trend. In some embodiments, the analytics module is configured to identify at least one trend based at least in part on the response from the set of responses and the indication.

Aspects of the systems, devices, and methods described herein are further operable to identify remedial measures based on the monitoring of ingestion of the substance, such as, for example, upon determination of noncompliance. In some embodiments, a non-transitory processor-readable medium stores code representing instructions to cause a processor to monitor, for a predetermined time period, a sensor for a sensor signal indicative of ingestion of a substance by a user. The code further includes code to cause the processor to, in response to not receiving an indication within the predetermined time period that the sensor received the sensor signal, generate a query including a first set of responses, and transmit the query to the user upon expiration of the predetermined time period. The code further includes code to cause the processor to receive, in response to transmitting the query, a selection of a response from the set of responses indicative of a reason of noncompliance of the user with a therapeutic regimen associated with the substance. The code further includes code to cause the processor to identify, based on the response from the set of responses, a remedial communication associated with the therapeutic regimen, and transmit the remedial communication to the user based on the response from the set of responses.

In some embodiments, the set of responses is a first set of responses. The code can further include code to cause the processor to, after receiving the selection of the response from the set of responses, modify the first set of responses to remove the response from the first set of responses to define a modified first set of responses, and generate a modified query including the modified first set of responses. In some embodiments, the code further includes code to cause the processor to transmit the modified query and receive a selection of a response from the modified first set of responses different from the response from the first set of responses. In some embodiments, the code further includes code to cause the processor to, when the response from the modified first set of responses indicates user intent to provide additional user input, transmit a second set of responses associated with the response from the modified first set of responses.

In some embodiments, the predetermined time period is a first predetermined time period. The code can further include code to cause the processor to store the response from the set of responses in a database and, when the sensor signal meets a criterion indicative of detection of ingestion of the substance during a second predetermined time period, generate an indication. In some embodiments, the code further includes code to cause the processor to store the indication in the database, and analyze at least one or more of the response from the set of responses or the stored indication to identify a trend.

In some embodiments, the predetermined time period is a first predetermined time period. The code can further include code to cause the processor to transmit, during a second predetermined time period after the first predetermined time period, a reminder to the user to ingest the substance within the second predetermined time period. In some embodiments, the code further includes code to cause the processor to transmit information associated with the response from the set of responses to at least one of the user, a caregiver of the user, a healthcare provider of the user, or an entity associated with the substance (e.g., a manufacturer of the substance).

Aspects of the systems, devices, and methods described herein are further operable to identify, based on user input, the reason(s) for nonadherence by the user. In some embodiments, a method includes monitoring a sensor for a sensor signal indicative of ingestion of a substance by a user, and in response to not receiving an indication within a predetermined time period that the sensor received the sensor signal, generating a query including a first set of responses. Each response from the first set of responses can be associated with a different second set of responses. The method further includes receiving, in response to transmitting the query to the user, an indication of a selection of a response from the first set of responses, and identifying the second set of responses associated with the response from the first set of responses. The method further includes transmitting, in response to receiving the response from the first set of responses, the second set of responses associated with the response from the first set of responses. The method further includes receiving, in response to transmitting the second set of responses associated with the response from the first set of responses, a selection of one or more responses from the second set of responses associated with the response from the first set of responses. The one or more responses from the second set of responses provides an explanation as to why the sensor did not receive the sensor signal within the predetermined time period.

In some embodiments, the method further includes, after receiving the selection of the response from the first set of responses, removing the response from the first set of responses to define a modified first set of responses and generating a modified query including the modified first set of responses. In some embodiments, the method further includes transmitting the modified query to the user, and receiving a selection of a response from the modified first set of responses different from the response from the first set of responses. In some embodiments, the method further includes, when the response from the modified first set of responses indicates user intent to provide additional user input, transmitting to the user the second set of responses associated with the response from the modified first set of responses.

In some embodiments, the method further includes performing one or more actions based on at least one of the response from the first set of responses or the one or more responses from the second set of responses. In some embodiments, the method further includes identifying a remedial communication associated with at least one of the response from the first set of responses or the one or more responses from the second set of responses. In some embodiments, the method further includes transmitting the remedial communication to the user.

In some embodiments, the method further includes transmitting, based on at least one of the response from the first set of responses or the one or more responses from the second set of responses, information associated with at least one of the response from the first set of responses or the one or more responses from the second set of responses to at least one of the user, a caregiver of the user, a healthcare provider of the user, or an entity associated with the substance. In some embodiments, the method further includes storing in a database at least one of the response from the first set of responses or the one or more responses from the second set of responses.

In some embodiments, the predetermined time period is a first predetermined time period and the sensor signal is a first sensor signal. The method can further include storing in a database at least one of the response from the first set of responses or the one or more responses from the second set of responses. In some embodiments, the method further includes generating an indication in response to receiving a second sensor signal indicative of detection of ingestion of the substance within a second predetermined time period. In some embodiments, the method further includes storing the indication in the database, and analyzing at least one or more of the stored response from the first set of responses, the stored one or more responses from the second set of responses, or the stored indication.

As used in this specification, the singular forms "a," "an" and "the" include plural referents unless the context clearly dictates otherwise. Thus, for example, the term "a network" is intended to mean a single network or a combination of networks.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor) capable of performing one or more specific functions associated with that module.

FIG. 1 is a schematic illustration of an environment and/or system for assessing non-adherence to a medication regimen. Such a system includes a compute device 100, a sensor 110, and a server 120.

The compute device 100, the sensor 110, and the server 120 can be in communication as indicated by solid lines in FIG. 1 via, for example, one or more networks. Such networks can be any type of network such as, for example, a local area network (LAN), a wide area network (WAN), a virtual network, a telecommunications network, and/or the Internet, implemented as a wired network and/or a wireless network (e.g., using a Bluetooth protocol). Any or all communications can be secured (e.g., encrypted) or unsecured.

The sensor 110 can be any device that can detect ingestion of a substance in any suitable manner, and generate an output based on the detection. In some embodiments, the sensor 110 can be associated with the body of a user ingesting the substance. In such embodiments, for example, the sensor can be wholly or partially implanted in the body of the user, topically applied to the body of the user, attached to a garment of the user, be within physical proximity of the user without physical contact, and/or the like. In some embodiments, the sensor 110 is configured to detect ingestion by detecting a signal emitted by the substance such as, but not limited to, a radio frequency (RF) signal, an electrical current, an acoustic signal, a body-transmissible signal, and/or the like. In some embodiments, the sensor 110 is configured as a receiver and/or detector for the signal emitted by the substance.

The sensor 110 can include any suitable hardware and/or software components such as, for example, antenna and/or electrodes for detecting a signal, a processor for processing the signal, a memory and/or database for storing the detected and/or processed signal, communication module(s) for communicating with other networks and/or devices (e.g., a Bluetooth and/or RF communication module, a wired communication module, and/or the like), a protective component, an adhesive component, and/or the like.

In some embodiments, the sensor 110 is configured to receive an encoded signal from one or more of a pharma-informatics enabled pharmaceutical composition (e.g., as described in PCT application Serial No. US2006/016370), an ingestible event marker (e.g., as described in provisional application Ser. No. 60/949,223), a parenteral device (e.g., as described in PCT/US2007/15547), and/or a variant thereof. The disclosure of each of these references is incorporated herein by reference in the entirety. In some embodiments, the sensor 110 is configured to be part of a receiver, as described in PCT Application No. PCT/US07/24225, or U.S. application Ser. No. 11/776,480, the disclosure of each of which is incorporated herein by reference in the entirety.

The server 120 can be a web server, a communication server, a personal computer, a work station, a tablet, a mobile device, a cloud computing environment, and/or the like. The server 120 includes a processor 142, a memory 144, and a communication module 146. In some embodiments, the server 120 can include a database storing compliance/noncompliance information (described in further detail herein), which can additionally or alternatively be stored in the memory 144. In some embodiments, the database is included in the memory 144. In other embodiments, the database is separate and/or distinct from the memory 144. The memory 144 can store instructions to cause the processor 142 to execute modules, processes and/or functions associated with the server 120. In some embodiments, the server 120 is configured to communicate with the compute device 100 and other devices (e.g., associated with a caregiver of a user) via the communication module 146 (e.g., a network interface device and/or other hardware and/or software used to connect the server 120 to a network). In some embodiments, the server 120 can store, transmit and/or manipulate the compliance/noncompliance information.

Figure 2:
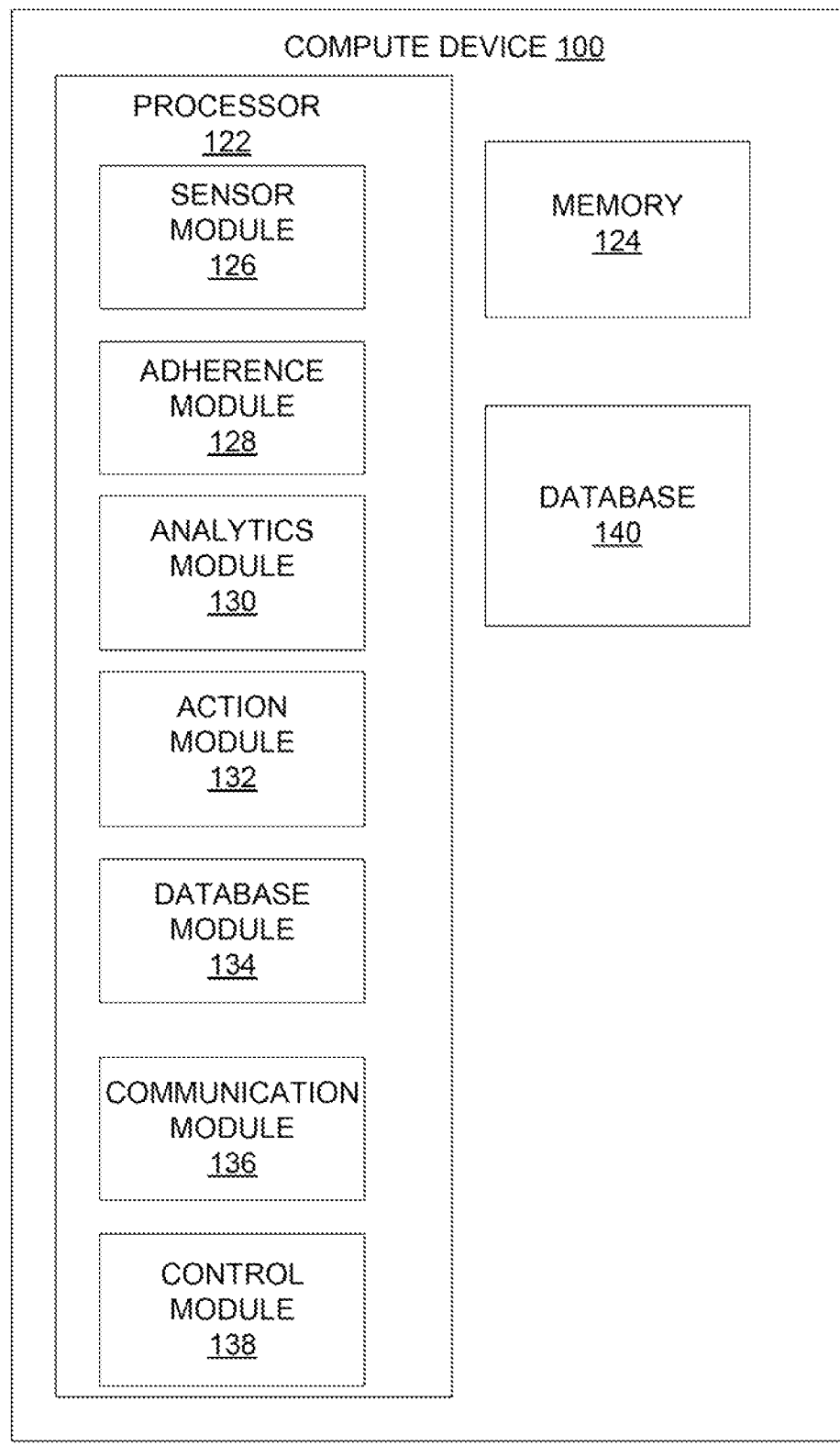
FIG. 2 is an illustration of the compute device of FIG. 1, according to an embodiment.

The compute device 100 can be a personal computer, a server, a work station, a tablet, a mobile device, a cloud computing environment, and/or the like. As illustrated in FIG. 2, the compute device 100 includes at least a processor 122 and a memory 124. FIG. 2 also illustrates a database 140, although it will be understood that, in some embodiments, the database 140 and the memory 124 can be a common data store. In some embodiments, the database 140 constitutes one or more databases. Further, in other embodiments (not shown), at least one database can be external to the compute device 100; for example, the database 140 can be part of the server 120.

The memory 124 and/or the database 140 can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory 124 and/or the database 140 can store instructions to cause the processor 122 to execute modules, processes and/or functions associated with the compute device 100. In some embodiments, memory 124 and/or the database 140 can store patient information.

The processor 122 can be, for example, a general purpose processor, a Field Programmable Gate Array (FPGA), an Application Specific Integrated Circuit (ASIC), a Digital Signal Processor (DSP), and/or the like. The processor 122 can be configured to run and/or execute application processes and/or other modules, processes and/or functions. Any of the sensor 110 and/or the server 120 can also includes a memory and a processor (not shown).

The processor 122 includes a sensor module 126, an adherence module 128, an analytics module 130, an action module 132, a database module 134, a communication module 136, and a control module 138. In some embodiments, the processor 122 can include additional modules (not shown). Each module can independently be a hardware module and/or a software module (implemented in hardware, such as the processor 122). While shown and described here as being implemented in processor 122, it is understood that any module(s) can be partially or entirely implemented in another hardware portion of the compute device 100, such as, for example, in an additional processor (not shown). For another example, communication module 136 can be implemented in processor 122 and can be used to control an antenna (not shown in FIG. 2) or a network interface device (not shown).

In some embodiments, the functionality of one or more of the modules can be combined and/or overlap. In some embodiments, the functionality of one or more modules and/or the interaction between the modules can be based on regulatory requirements for data processing, storage, integrity, security, and/or the like.

The control module 138 interfaces with a user of the compute device 100, control and/or otherwise generally interact with the compute device 100 to control operating parameters (e.g., settings) of other modules. In some embodiments, for example, a user can input commands and/or instructions to the compute device 100 via the control module 138.

The sensor module 126 can monitor the sensor 110 for a sensor signal indicative of ingestion of a substance by a user associated with the sensor. In some embodiments, the sensor module includes, monitors or is used to control a communication link between the compute device 100 and an antenna (e.g., via an antenna, wired connection, etc. associated with the communication module 136). Specifically, the sensor module 126 can monitor a communication component (e.g., a Bluetooth antenna, an RFID antenna, wired connection and/or the like) of the compute device 100 for the sensor signal provided by the sensor 110. In some embodiments, the sensor signal is one or more of a wireless signal (e.g., RF signal, a Bluetooth signal, an acoustic signal, and/or the like) or a wired signal (e.g., an electric current). The sensor signal can include any suitable, ingestion-related information such as, but not limited to, identification of the substance(s) ingested, timing of ingestion, indication of the quantity of substance(s) ingested, serial number associated with a specific instance of substance(s) ingested, lot of substance(s) ingested, and/or the like.

In some embodiments, the sensor signal is substantially continuously received by the sensor module 126, while in other embodiments, the sensor signal is intermittently received and consumed by the sensor module such as upon, for example, a synchronization step carried out between the sensor 110 and the sensor module 126. The transmission of the sensor signal can be initiated by the sensor 110 (e.g., upon detecting an ingestion event), by the sensor module 126, or both.

In some embodiments, the sensor signal is transmitted by the sensor 110 and received by the sensor module 126 substantially immediately following ingestion is detected by the sensor. In other embodiments, the receipt of the sensor signal at the sensor module 126 is delayed with respect to the ingestion event. In such an embodiment, the sensor 110 can store information associated with one or more ingestion events. The sensor 110 can then transmit the sensor signal with the information at a later time and upon synchronization with the sensor module 126.

In some embodiments, the sensor module 126 communicates information associated with the monitored sensor signal to the adherence module 128. The communicated information can include, but is not limited to, the monitored sensor signal, an indication of receipt and/or start of receipt of the monitored sensor signal, an indication of absence and/or terminal of receipt of the monitored sensor signal, an indication of a signal property of the monitored sensor signal (e.g., the signal strength), and/or the like. In some embodiments, when the sensor signal fails to meet a signal criterion (e.g., the sensor signal is below a minimum strength or is undetectable, and/or the like), the sensor module does not communicate sensor signal to the adherence module 128, and further does not communicate any information related to ingestion to the adherence module.

The adherence module 128 is configured to analyze the sensor signal and/or the information associated with the monitored sensor signal received from the sensor module 126 to determine compliance of the user with a therapeutic regimen associated with the substance. The therapeutic regimen can include, for example, a specification of one or more substances, an amount/dose associated with the substance(s), a dosing schedule associated with the substance(s), and/or the like. In some embodiments, the therapeutic regimen includes a specification of a predetermined time period within which the sensor signal should be received, such as, for example, a moving time window, every 24 hours, a time window based on a time of day, an amount of time after detecting a previous ingestion, an amount of time after receiving a notification that ingestion was not detected, an amount of time after presenting a reminder to a patient to take their medication, and/or the like. In some instances, for example, the predetermined time period can be 12 hours from 6 o'clock in the morning (i.e., between 6:00 am and 6:00 pm), the predetermined time period can be 30 hours from a previous detection of ingestion, the predetermined time period can be 24 hours from a previous notification of not receiving a signal associated with ingestion, 24 hours after presenting a reminder to the patient to take the medication, and/or any other suitable predetermined time period.

The therapeutic regimen can be accessible to the adherence module 128 in any suitable manner such as, for example, via storage in the memory 124, storage on the database 140 (accessible via the database module 134), storage on the server 120, and/or the like. In some embodiments, the therapeutic regimen is associated with the patient information. The therapeutic regimen can be entered at the compute device 100 (e.g., via the control module 138), or received from another device directly or indirectly (e.g., via the server 120).

In some embodiments, the adherence module 128 is configured to analyze the sensor signal and/or the information associated therewith to identify ingestion information such as, but not limited to, one or more of date of ingestion, time of ingestion, an identification of medication(s) ingested, the quantity/dosage of medication(s) ingested, the number of units of medication(s) ingested, the source of the medication(s) ingested (e.g., manufacturer, distributor, dispensing pharmacy, etc.), the lot/batch number of the medication(s) ingested, and/or the like. In some embodiments, the adherence module 128 compares the analysis results against the therapeutic regimen to determine whether the user is in compliance with the therapeutic regimen. For example, the therapeutic regimen can specify that a medication must be ingested at a prescriber-specified frequency (e.g., every 24 hours, at a certain time of day, within a certain time period after the prior detection of ingestion, within a certain time period after presenting a reminder to the patient, etc.) for the user to be deemed compliant, and the adherence module can compare the time of ingestion based on the sensor signal to ensure the sensor signal is received within 12-48 hours of the last time the user consumed the substance. In some embodiments, the adherence module 128 is configured to generate a reminder for the user to ingest the substance based on the therapeutic regimen such as, for example prior to and/or during the predetermined time period for each predetermined time period.

In some embodiments, if the adherence module 128 determines that the sensor signal is not received by the sensor module 126 and/or generally does not meet the sensor criterion, in the predetermined time period, the adherence module 128 can generate a query (also referred to as a "notification") indicative of noncompliance of the user with the therapeutic regimen associated with the substance. The query can be directed to gather user input on the reason(s) for noncompliance. In some embodiments, the query can include a question such as, for example, "what is the reason you did not take the medication?".

In some embodiments, the query includes a set of primary responses or potential primary responses that can characterize the various reasons a user might have been noncompliant. In some embodiments, the set of primary responses can generally account for one or more of user error (e.g., "I forgot"), inability (e.g., "I couldn't", or "I ran out of medication"), deliberate action (e.g., "I didn't feel like it", or "The medication is not helping"), ingestion that deviated from the therapeutic regimen (e.g., "I took it after midnight"), errors in receipt of the sensor signal (e.g., "I took the medication as directed"), and/or the like. The set of primary responses can be presented to the user within the question and the user can select a response from the set of primary responses. In some embodiments, the set of responses is programmable, via the control module 138 and/or via instructions received from the server 120.

In some embodiments, the adherence module 132 can, in response to receiving a selection of a response from the primary set of responses from the communication module 134 (described in more detail below), identify a secondary set of responses associated with the response from the primary set of responses. In this manner, the adherence module 132 can follow up on the user's selected primary response with a more detailed listing of reasons (i.e., the secondary set of responses) for noncompliance that are associated with the selected response. For example, if the selected primary response "I didn't feel like it", the secondary set of responses can include "I don't need medication", "medication doesn't help", "family or friends do not support my taking medication" (not shown in FIG. 5), "heard or read bad things about medication, e.g., books, internet," (not shown in FIG. 5) other reasons, and/or the like. In some embodiments, the adherence module 132 can store the selected primary response and/or the selected secondary response in the memory 124 and/or the database 140 (e.g., via the database module 134). In some embodiments, the secondary set of responses is programmable, for example, via the control module 138 and/or via instructions received from the server 120.

In some embodiments, the adherence module 132, can, in response to receiving a selection of a primary response from the communication module 134 (described in more detail below), remove the selected primary response from the primary set of responses to define a modified primary set of responses. In some embodiments, the adherence module 132 can generate a modified query including the modified primary set of responses. In this manner, the adherence module 132 can account for a user's initial response while being mindful that there may be additional reasons (other than the selected response) for the user's noncompliance, and can accordingly generate a modified query to present to the user.

In some embodiments, the modified primary set of responses is generated upon receiving a selection of a secondary response. In this manner, the adherence module 132 can ensure that a secondary response is provided by the user based on the user's initial response from the primary set of responses (via the user's selected secondary response from the secondary set of responses) before modifying the query and asking the user if other reasons for noncompliance apply. The level of information/detail can be predetermined, and be generally based on the information requested by and/or desired for a third party, such as a caregiver, to understand the context/reasoning for noncompliance. In some embodiments the user can be permitted to select a single response from the secondary set of responses, while in other embodiments, the user can be permitted to select more than one response from the secondary set of responses.

The communication module 136 can transmit the query (including the set of responses) generated by the adherence module 132 to the user in any suitable manner that permits the user to perceive and respond to the query. For example, the communication module 136 can transmit the query to a display interface (not shown) of the compute device 100, to a speaker (not shown) of the compute device 100, to another device (not shown) associated with the user (e.g., via a network), and/or the like. In some embodiments, the query can be transmitted to the user after and/or in response to expiration of the predetermined time period, while in other embodiments, the query can be transmitted to the user prior to expiration of the predetermined time period.

The query can be presented to the user in any suitable format, including visual, audio, and/or the like. In some embodiments, the query is visually presented to the user as a selectable list of responses. In some embodiments the user can be permitted to select a single response. In other embodiments, the user can be permitted to select more than one response.

The communication module 136 can receive, in response to the user selecting a response, an indication of the selection of the response from the primary set of responses. In some embodiments, the communication module 136 can communicate the selected response to the adherence module 132, and to receive a modified query with the selected response removed in return, as described above. In some embodiments, the communication module 136 can transmit the modified query to the user, and can receive a selection of a response from the modified primary set of responses different from the response from the primary set of responses.

In some embodiments, when the response from the modified primary set of responses indicates user intent to provide additional user input (e.g., the user picks a response other than "no" when the modified query asks "is there another reason?"), the communication module 136 can transmit to the user a secondary set of responses that is associated with the response from the modified primary set of responses. In some embodiments, the communication module 136 is further configured to receive, in response to transmitting the secondary set of responses associated with the response from the primary set of responses, a selection of one or more responses from the secondary set of responses associated with the response from the primary set of responses. The one or more responses from the secondary set of responses can provide an explanation and/or additional detail as to why the sensor did not receive the sensor signal within the predetermined time period.

In some embodiments, the response(s) to the primary set and/or the secondary set of responses can be stored, such as in the database 140 by the database module 134. The stored response(s) can then be analyzed for various purposes such as, but not limited to, historical analysis, predictive/prophetic determination of future compliance and/or noncompliance, analysis to determine one or more trends associated with the user, statistical information, and/or the like.

The analytics module 130 is configured to identify at least one trend associated with compliance and/or noncompliance of the user with the therapeutic regimen. Such trends can include, for example, compliance frequency as a percentage, a number of times a user has provided a specific response from the set of responses when queried about noncompliance, the progress of the user's treatment, combinations thereof, and/or the like. In some embodiments, the trend is based on the selected response from the primary and/or secondary set of responses such as, for example, whether the user has selected a response more than a predetermined number of times and/or at a predetermined frequency.

In some embodiments, the trend is based on timing information associated with the selected response from the primary and/or secondary set of responses such as, for example, if the user specifies he took the medication at a later time. In some embodiments, the trend is based on timing information associated with historical data of compliance of the user with the therapeutic regimen such as, for example, if the user has missed an evening dose more frequently than a morning dose in a twice daily regimen.

In some embodiments, the trend is based on frequency information associated with the selected response from the set of responses, such as, for example how often the user has selected a response. In some embodiments, the trend is based on frequency information associated with historical data of compliance of the user with the therapeutic regimen such as, for example, if the user has been deemed noncompliant more than twice in a week.

In some embodiments, the trend is based on at least one of the selected response from the primary and/or secondary set of responses, timing information associated with the response from the primary and/or secondary set of responses, timing information associated with historical data of compliance of the user with the therapeutic regimen, frequency information associated with the response from the primary and/or secondary set of responses, or frequency information associated with historical data of compliance of the user with the therapeutic regimen.

In some instances no sensor signal is received by the adherence module 128 during a first predetermined time period (e.g., based on the sensor module 126 not receiving a sensor signal from the sensor 110), and the adherence module 128, as noted earlier, generates and transmits a primary query to the user along with the primary set of responses after the first predetermined time period, such as in a second predetermined time period. The adherence module 128 can further generate and transmit a secondary query to the user in response to a selected primary response. In such instances, if the sensor module receives a sensor signal indicative of detection of ingestion of the substance within the second predetermined time period, such as a time period after the first predetermined time period, the adherence module 128 can generate an indication associated with the detection of ingestion of the substance during the second predetermined time period. In some embodiments, the database module 134 can store, in the memory 124 and/or the database 140, the response from the set of responses (from the first predetermined time period), as well as a indication of ingestion of the substance during the second predetermined time period).

In some embodiments, the analytics module 130 can retrieve the response from the set of responses and the indication from the memory 124 and/or the database 140 prior to the analytics module identifying at least one trend.

In some embodiments, the analytics module 130 can identify the at least one trend based at least in part on the response from the set of responses and the indication. In some embodiments, the analytics module 130 can analyze at least the response(s) from the primary set of responses, the response(s) from the secondary set of responses, or the indication. In some instances, for example, the analytics module 130 can identify noncompliance and/or compliance trends based on the day of the week, time of day, frequency of one or more particular responses, comparison with instances and/or patterns of compliance/noncompliance observed in other users of the substance, and/or the like. For example, the analytics module 130 can determine that a user may often be depressed on Monday, and thus a trends exists that they do not take their medication on Monday because of this depression. For another example, the analytics module 130 can determine that a user often indicates that on Wednesday he does not have a ride to refill a prescription and thus does not take his medication. As discussed in further detail herein, the action module 132 can notify a user, family member, medical professional, care giver and/or the like of the trends. Such notifications can be used to assist the user in reversing trends associated with noncompliance.

In some embodiments, the modules of the compute device 100 can transmit, in response to not receiving an indication of ingestion, during a first predetermined time period, a reminder to the user to ingest the substance within a second predetermined time period. For example, the adherence module 128 can generate the reminder during the second predetermined time period, and the communication module 136 can transmit the reminder to the user. The second predetermined time period can be any time period after the first predetermined time period. In this manner, the communication module 136 can provide a reminder to the user to ingest the substance subsequent to a noncompliance event.

The action module 132 can perform one or more actions based on the response selected from a primary set of responses. The one or more actions can be any activity associated with the selected response, and can be triggered by virtue of the selection of the response and/or a trend identified by the adherence module 128. In some embodiments, the action includes identifying remedial communication associated with the selected response. Similarly stated, in some embodiments, the action module 132 can identify remedial communication associated with the selected response, which can then be transmitted to the user (e.g., via the communication module 136) based on a response selected from the primary and/or secondary set of responses. A remedial communication can be any suitable communication that addresses a selected response and/or a trend identified based on the selected response. For example, if the user selects "I didn't feel like taking my medication", the remedial communication can include information illustrating the risks associated with permanently and/or temporarily stopping therapy. As another example, if the user selects "The medication is not helping", the remedial communication can include studies that illustrate the benefits of the medication. For yet another example, if the a trend is identified that the user sometimes fails to take their medication on Wednesday because they do not have a ride to refill a prescription, a notification can be provided with information on mail-order prescriptions and/or a reminder can be provided on earlier in the week to refill their prescription prior to Wednesday.

In some embodiments, the action module 132 can provide literature to another entity (e.g., the caregiver and/or the prescriber) on how to counsel the patient based on the response(s). In some embodiments, the action module 132 can search (e.g., via crawling, spidering, and/or the like) the internet and/or trusted sources such as trusted database to identify the remedial communication and the literature. In some embodiments, the action module 132 can populate the memory 124 and/or the database 140 with the search results.

In some embodiments, the action includes notifying an entity associated with the user about the selected response and/or a trend associated with the response (e.g., via the communication module 136). For example, in some embodiments, the action module 132 can transmit, via the communication module 136, information associated with the response from the set of responses to at least one of the user, a caregiver of the user, a healthcare provider of the user, or an entity associated with the substance (e.g., a manufacturer, a distributor, a pharmacy, and/or the like). The action can be triggered by a single incident of noncompliance, or by a trend/pattern of noncompliance. In some embodiments, the trigger for the action can be specified and/or programmed by another entity such as a manufacturer of the substance, or a prescriber (e.g., interfacing with the compute device 100 via the control module 138).

Figure 3:
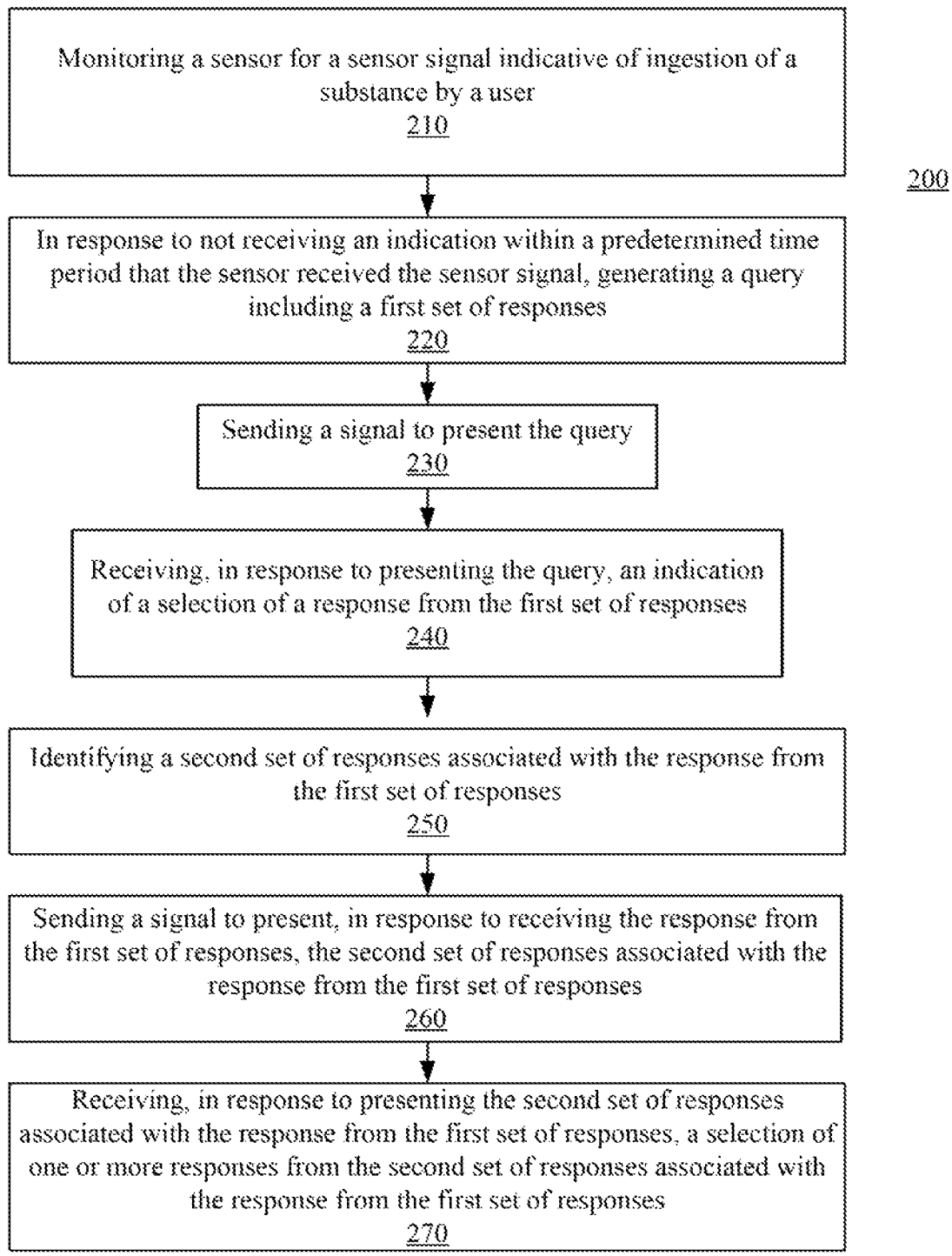
FIG. 3 is a flowchart illustrating a method of event sensing and analysis, according to an embodiment.

FIG. 3 illustrates a method 200 of assessing nonadherence to a medication regimen. In some embodiments, the method 200 can be executed by a device structurally and/or functionally similar to the compute device 100, shown and described with respect to FIGS. 1-2. The method 200 includes, at 210, monitoring a sensor for a sensor signal indicative of ingestion of a substance by a user.

The method 200 further includes, at 220, in response to not receiving an indication within a predetermined time period that the sensor received the sensor signal, generating a query including a first set of responses. Each response from the first set of responses can be associated with a different second set of responses.

The method 200 further includes, at 230, transmitting the query to the user. The method 200 further includes, at 240, receiving, in response to transmitting the query to the user, an indication of a selection of a response from the first set of responses.

The method 200 further includes, at 250, identifying a second set of responses associated with the response from the first set of responses. The method 200 further includes, at 260, transmitting, in response to receiving the response from the first set of responses, the second set of responses associated with the response from the first set of responses.

The method 200 further includes, at 270, receiving, in response to transmitting the second set of responses associated with the response from the first set of responses, a selection of one or more responses from the second set of responses associated with the response from the first set of responses. In some embodiments, the one or more responses from the second set of responses can provide an explanation as to why the sensor did not receive the sensor signal within the predetermined time period. In some embodiments, the method 200 further includes storing in a database at least one of the response from the first set of responses or the one or more responses from the second set of responses.

In some embodiments, the method 200 further includes, after receiving the selection of the response from the first set of responses at 240, removing the response from the first set of responses to define a modified first set of responses (not shown in FIG. 3). In some embodiments, the method 200 further includes generating a modified query that includes the modified first set of responses. In some embodiments, the method 200 further includes transmitting the modified query to the user, and receiving a selection of a response from the modified first set of responses different from the response from the first set of responses. In some embodiments, when the response from the modified first set of responses indicates user intent to provide additional user input, the method 200 further includes transmitting to the user the second set of responses that is associated with the response from the modified first set of responses. In some embodiments, the method 200 further includes performing one or more actions based on at least one of the response from the first set of responses or the one or more responses from the second set of responses.

In some embodiments, the method 200 further includes identifying a remedial communication associated with at least one of the response from the first set of responses or the one or more responses from the second set of responses. In some embodiments, the method 200 further includes transmitting the remedial communication to the user.

In some embodiments, the method 200 further includes transmitting, based on at least one of the response from the first set of responses or the one or more responses from the second set of responses, information associated with at least one of the response from the first set of responses or the one or more responses from the second set of responses to at least one of the user, a caregiver of the user, a healthcare provider of the user, or an entity associated with the substance.

In some embodiments, the method 200 further includes storing in a database at least one of the response from the first set of responses or the one or more responses from the second set of responses. In some embodiments, in response to receiving a sensor signal indicative of detection of ingestion of the substance within a second predetermined time period after an initial predetermined time period, the method 200 further includes generating an indication. In some embodiments, the method 200 further includes storing the indication in the database, and analyzing at least one or more of the stored response from the first set of responses, the stored one or more responses from the second set of responses, or the stored indication.

Figure 4:
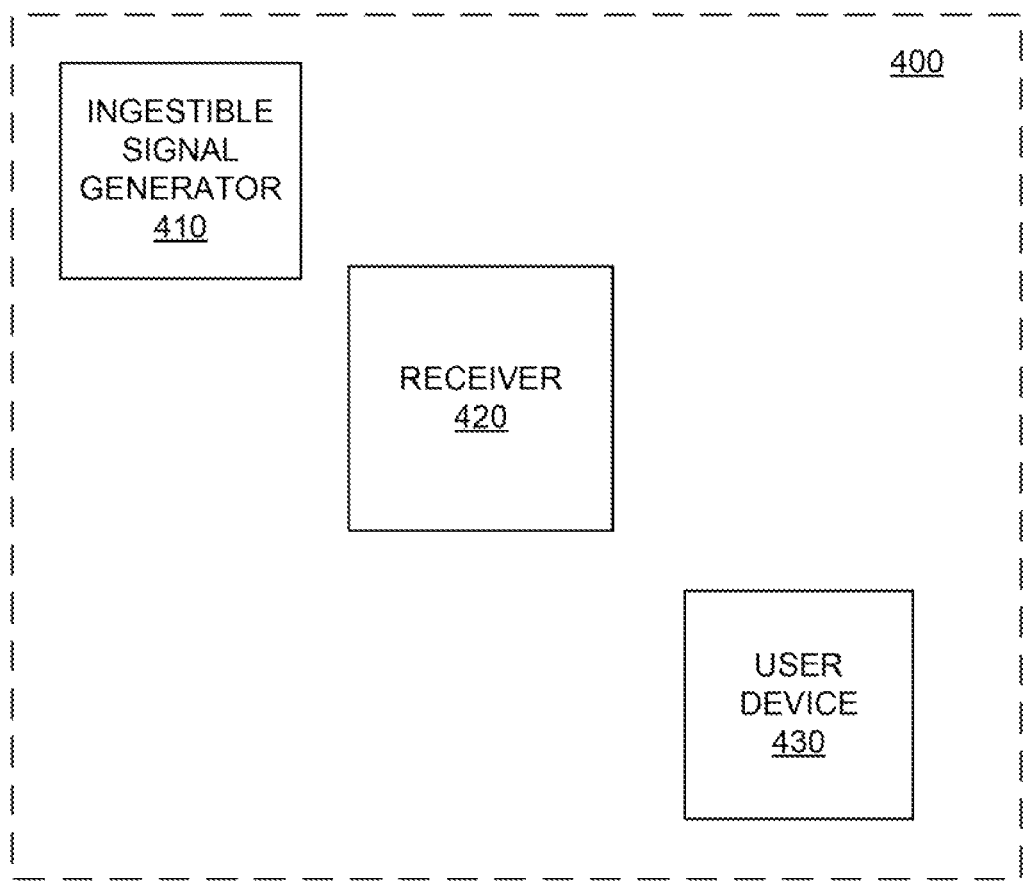
FIG. 4 is a system for event sensing and analysis, according to an embodiment.

FIG. 4 illustrates a system 400 for event sensing and analysis, according to embodiments. In some embodiments, the system 400 can include an ingestible signal generator coupled to a medication (collectively, "ingestible signal generator 410"). The ingestible signal generator 410 is configured to generate a body-transmissible signal upon ingestion by a user. In some embodiments, the ingestible signal generator 410 is similar to one or more of a pharma-informatics enabled pharmaceutical composition (e.g., as described in PCT application serial no. PCT/US2006/016370), an ingestible event marker (e.g., as described in provisional application Ser. No. 60/949,223), a parenteral device (e.g., as described in PCT application serial no. PCT/US2007/15547), and/or a variant thereof. For example, in some embodiments, the ingestible signal generator 410 includes an active agent such as a pharmaceutical substance, an identifier that emits a signal when it contacts a targeted site (e.g., a user's stomach), and a pharmaceutically acceptable carrier such as (but not limited to) corn starch or gelatin, lactose, dextrose, sucrose, microcrystalline cellulose, kaolin, mannitol, dicalcium phosphate, sodium chloride, alginic acid, and/or combinations thereof. As another example, in some embodiments, the ingestible signal generator 410 includes an ingestible event marker (i.e., an IEM). In some embodiments, the IEM includes an identifier, which may or may not be present in a physiologically acceptable carrier. The identifier can be characterized as being activable upon contact with a target internal physiological site of a body (e.g., a specific target environment, including a target chemical environment, target physical environment etc.), such as digestive tract internal target site.

In some embodiments, the ingestible signal generator 410 includes a power source (e.g., a battery) and/or a partial power source (e.g., two electrodes that use body fluid such as stomach acid as an electrolyte) configured to power a transmitter (e.g., a radio frequency (RF) transmitter, a conductive signal generator, and/or the like) when ingested. In some embodiments, the partial power source includes two dissimilar materials which constitute two electrodes. In some embodiments, the two dissimilar materials are shielded from the surrounding environment by an additional layer of material. When the shielding material (e.g., active agent/carrier matrix), is dissolved or eroded by the surrounding fluid, the electrode materials are exposed and come in contact with the body fluid, such as stomach acid or other types of electrolyte fluid. A potential difference/voltage is generated between the electrodes as a result of the oxidation and reduction reactions at the two electrode materials. A voltaic cell, or battery, can be thereby formed. Accordingly, in some embodiments, such batteries are configured such that when the two dissimilar materials are exposed to the target site, e.g., the stomach, the digestive tract, etc., during the physical and chemical erosion of the composition in which the signal generation element is present, a voltage is generated. As examples of dissimilar materials, copper and zinc when put into a cell have different potentials, as do gold and magnesium.

The transmitter of the ingestible signal generator 410 can then send and/or transmit a signal indicating that the medication has been ingested. In some embodiments, the transmitter component is made up of one or more coils. As such, the signal transmitter may include a variety of different transmitters, e.g., electrodes, antennas (e.g., in the form of wires) coils, etc. In some embodiments, the signal is transmitted either by one or two electrodes or by one or two wires. A two-electrode transmitter is a dipole; a one electrode transmitter forms a monopole.

The system 400 also includes a receiver 420 that is configured to be disposed on the body of the user during use. In some embodiments, the receiver 420 including a sensor configured to detect the body-transmissible signal. In some embodiments, the sensor of the receiver 420 can be structurally and/or functionally similar to the sensor 110. In some embodiments, the receiver 420 can be structurally and/or functionally similar to the receiver as described in PCT Application No. PCT/US07/24225, or U.S. application Ser. No. 11/776,480, the disclosure of each of which is incorporated herein by reference in the entirety. The receiver 420 is further configured to generate and wirelessly transmit a sensor signal based on the body-transmissible signal received from the ingestible signal generator 410.

The system 400 also includes a user device 430 that is associated with the user, and includes at least a processor and a memory. In some embodiments, the user device 430 can be structurally and/or functionally similar to the compute device 100 described herein. In some embodiments, the processor of the user device 430 is configured to wirelessly monitor the sensor of the receiver 420 for the sensor signal, and, in response to not receiving the sensor signal within a predetermined time period, generate a notification for the user. In some embodiments, the processor of the user device 430 is configured to send a signal to present the notification to the user and receive a response to the notification from the user. In some embodiments, the processor of the user device 430 is configured to identify at least one trend associated with the sensor signal and the medication based on the response, and based on a history associated with the medication. In some embodiments, the processor of the user device 430 is configured to perform one or more actions based on the response and at least one trend. In some embodiments, the processor of the user device 430 is configured to identify a communication associated with the response from the set of responses, and to send a signal to present the communication to the user.

Still referring to the user device 430 of FIG. 4, in some embodiments, the set of responses is a first set of responses, and the processor of the user device 430 is further configured to, in response to receiving the response from the first set of responses, remove the response from the first set of responses to define a modified first set of responses. In some embodiments, the processor of the user device 430 is further configured to generate a modified query including the modified first set of responses, and to send a signal to present the modified query to the user. In some embodiments, the processor of the user device 430 is further configured to receive a selection of a response from the modified first set of responses that is different from the response from the first set of responses. In some embodiments, the processor of the user device 430 is further configured to, when the response from the modified first set of responses includes an indication of additional user input, send a signal to present to the user a second set of responses associated with the response from the modified first set of responses.

In some embodiments, a kit (not shown) includes two or more of the ingestible signal generator 410, the receiver 420, and the user device 430. For example, in some embodiments, a kit includes at least the ingestible signal generator 410 and the receiver 420.

Figures 5A, 5B:
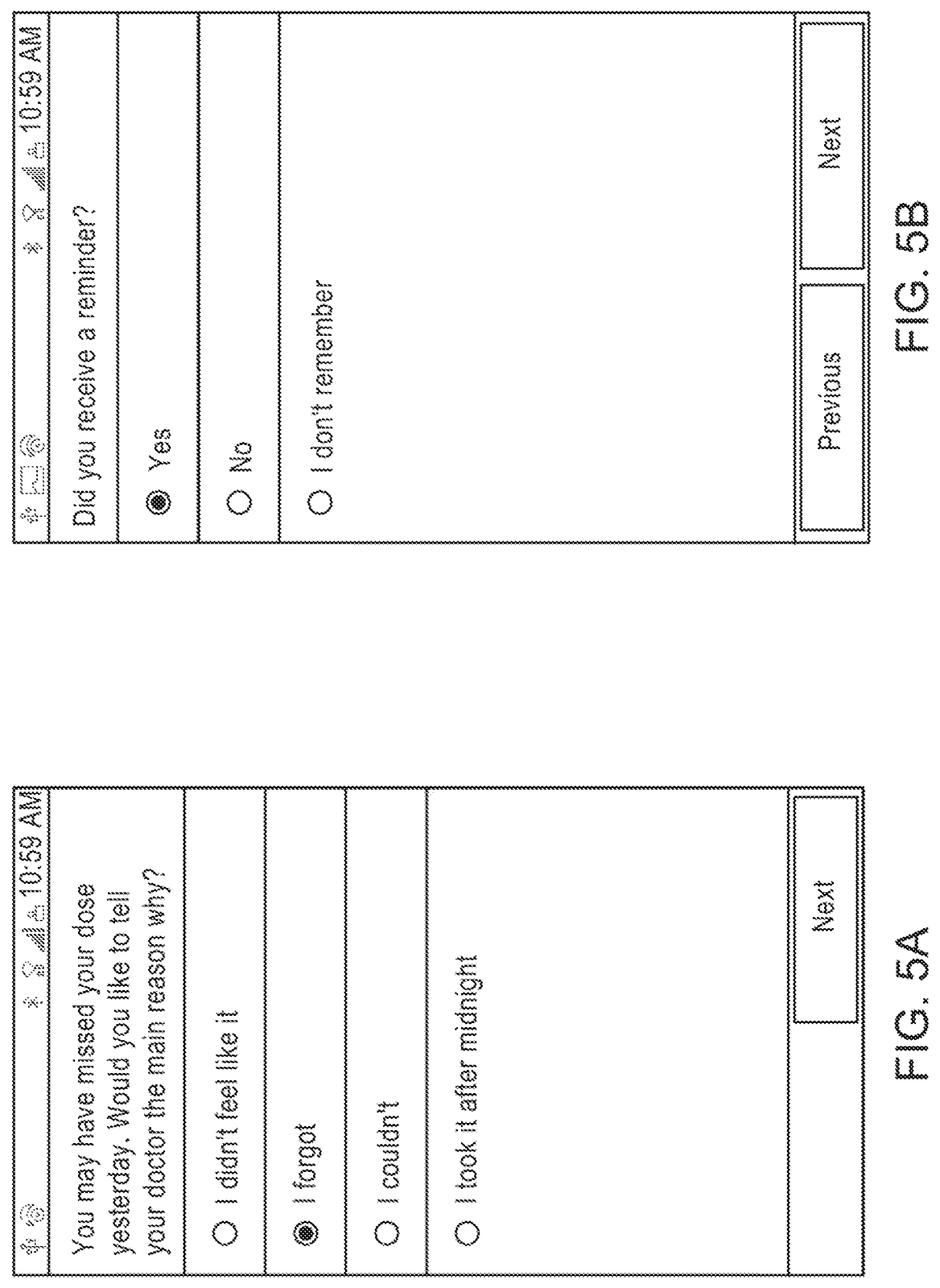
Figures 5C, 5D:
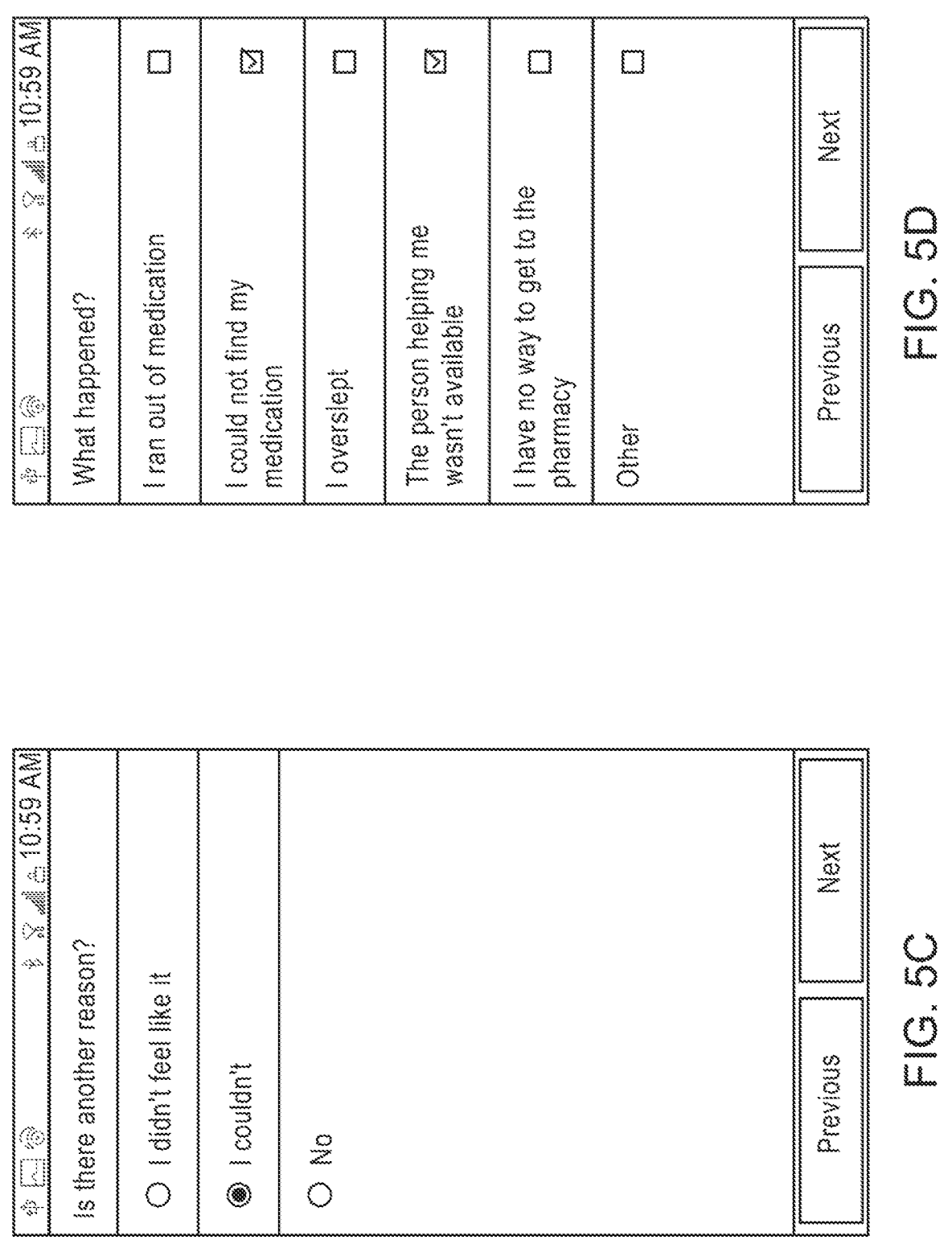
Figure 5E:
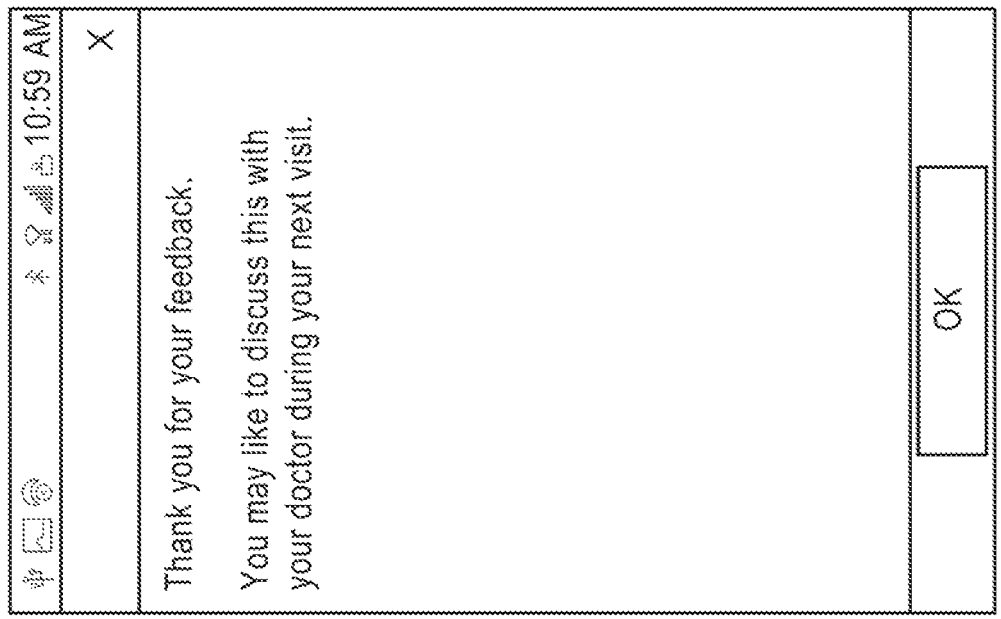

FIGS. 5A-5E are exemplary illustrations of interactive interfaces usable by a user of the compute device to provide information associated with nonadherence to a medication regimen. Explained with reference to FIGS. 1-4, FIG. 5A illustrates a query asking the user for a reason why they failed to comply with a therapeutic regimen (e.g., why they missed a dose of medication), such as can be generated by the adherence module 128 when no sensor signal is detected by the sensor 110 within an expected time period as defined by the therapeutic regimen. FIG. 5A also illustrates a list of selectable responses (similar to the primary set of responses described herein), where the user has selected the "I forgot" option. FIG. 5B illustrates a secondary query and a secondary set of responses based on the user's selection of the "I forgot" option, designed to ensure the user received a reminder to ingest the dose.

FIG. 5C illustrates an exemplary interface of a modified primary query with a modified primary set of responses that is provided to the user after receiving a selection of an initial primary response from the primary set of responses, and/or after receiving a selection of a secondary response from the secondary set of responses. The modified set of responses remove the previously selected response of "I forgot", and further includes the option of the user providing no additional input (i.e., the "no" option). If the user selects the "I didn't feel like it" or "I couldn't" options (i.e., indicates that he wishes to provide additional user input), a secondary set of responses that is associated with the selected response from the modified set of primary responses is provided to the user. For example, FIG. 5D illustrates a secondary set of responses associated with the "I couldn't" response in FIG. 5C, generally directed to determining why the user couldn't take the dose. FIG. 5E illustrates an acknowledgement screen that can be presented to the user, suggesting the user discuss the reason(s) for non-compliance. In other instances, a remedial communication, as described herein, can be selected and presented to the user based on the user's responses to the primary and/or secondary queries.

Figure 6:
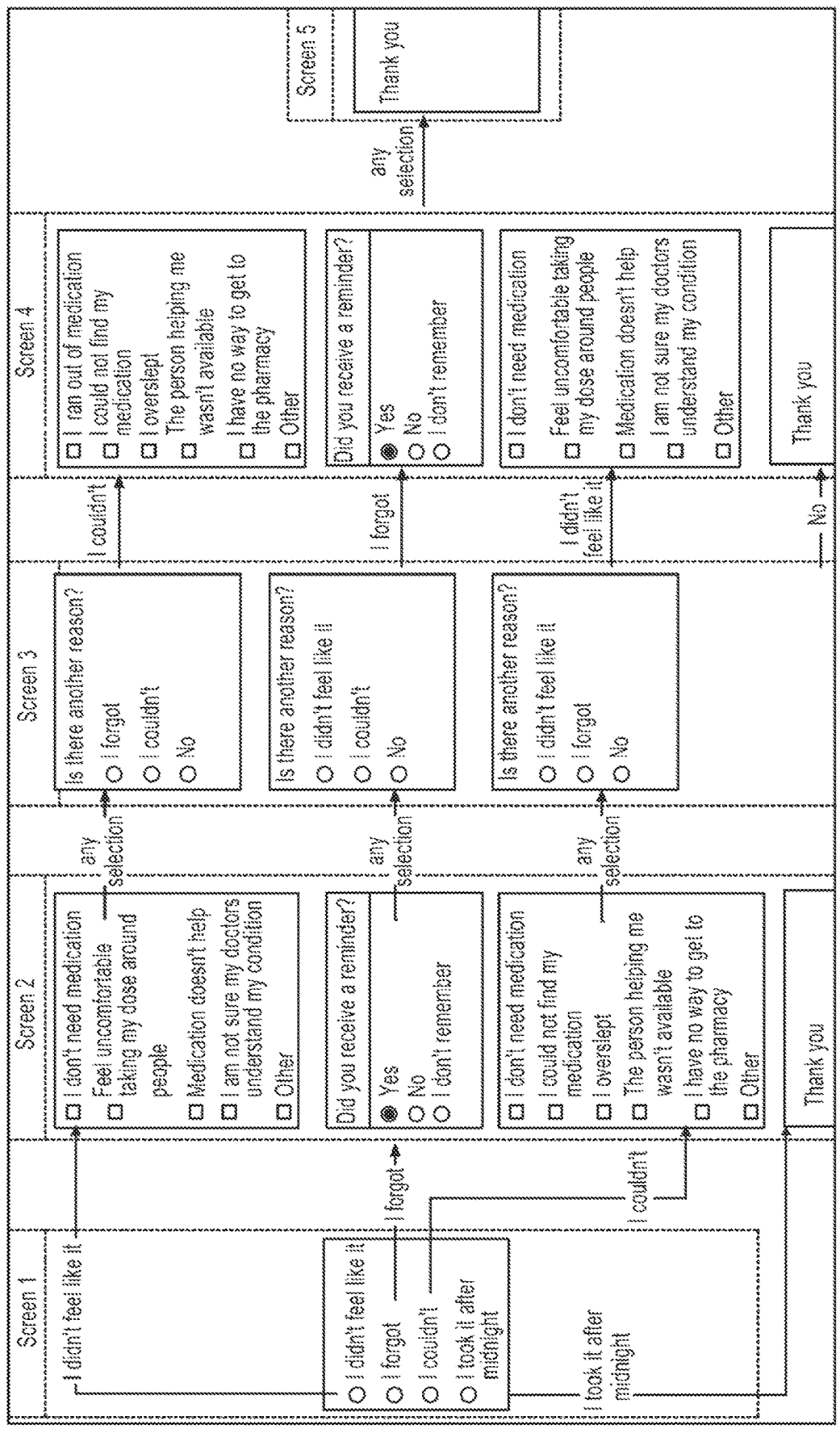
FIG. 6 is an exemplary flowchart of screenshots for assessing non-adherence, according to an embodiment.

FIG. 6 is an exemplary flowchart of responses as can be encountered by a user when noncompliance is detected. Upon determination of noncompliance (e.g., no ingestion signal received when expected per a therapeutic regimen), a primary set of responses ("Screen 1") is generated and transmitted to the user. Depending on the response selected from the primary set of responses, a secondary set of responses ("Screen 2") can be provided to the user that is based on the selected primary response. In some instances, the secondary set of responses request further user input. In some instances, depending on the response selected from the primary set of responses, an acknowledgement of receipt of the response selected from the primary set of responses, such as a "thank you" indication, can be provided. In the instance the secondary set of responses request further user input, after the user selects a response from the secondary set of responses, a modified primary set of responses ("Screen 3") can be generated and presented to the user. The modified primary set of responses removes the selected response from the primary set of responses, and additionally provides an option for the user to not provide additional input. As an example, if the user selects "I didn't feel like it" in Screen 1, then the Screen 3 presented to the user will exclude the "I didn't feel like it" option, and again present the "I forgot" and "I couldn't" options from Screen 1, and further present a "no" option. In this example, the "I took it after midnight" option from Screen 1 is not presented in a modified primary set of responses, since it is assumed that the user would have selected this response on Screen 1 to indicate he took the medication, albeit in a delayed manner. It is understood that in some embodiments, however, the "I took it after midnight" option can be presented as part of the modified primary set of responses as well.

If the user selects a response from the modified primary set of responses that requests additional input, a secondary set of responses ("Screen 4") based on the response selected from the modified primary set of responses is presented to the user. After the user makes a selection from the secondary set of responses of Screen 4, the system can acknowledge the user's input (see Screen 5). It is understood however, that in some embodiments (not shown), the approach exemplified in FIG. 6 can iterate as many times as desirable/necessary to capture user input regarding noncompliance, and can be, for.

Figure 7:
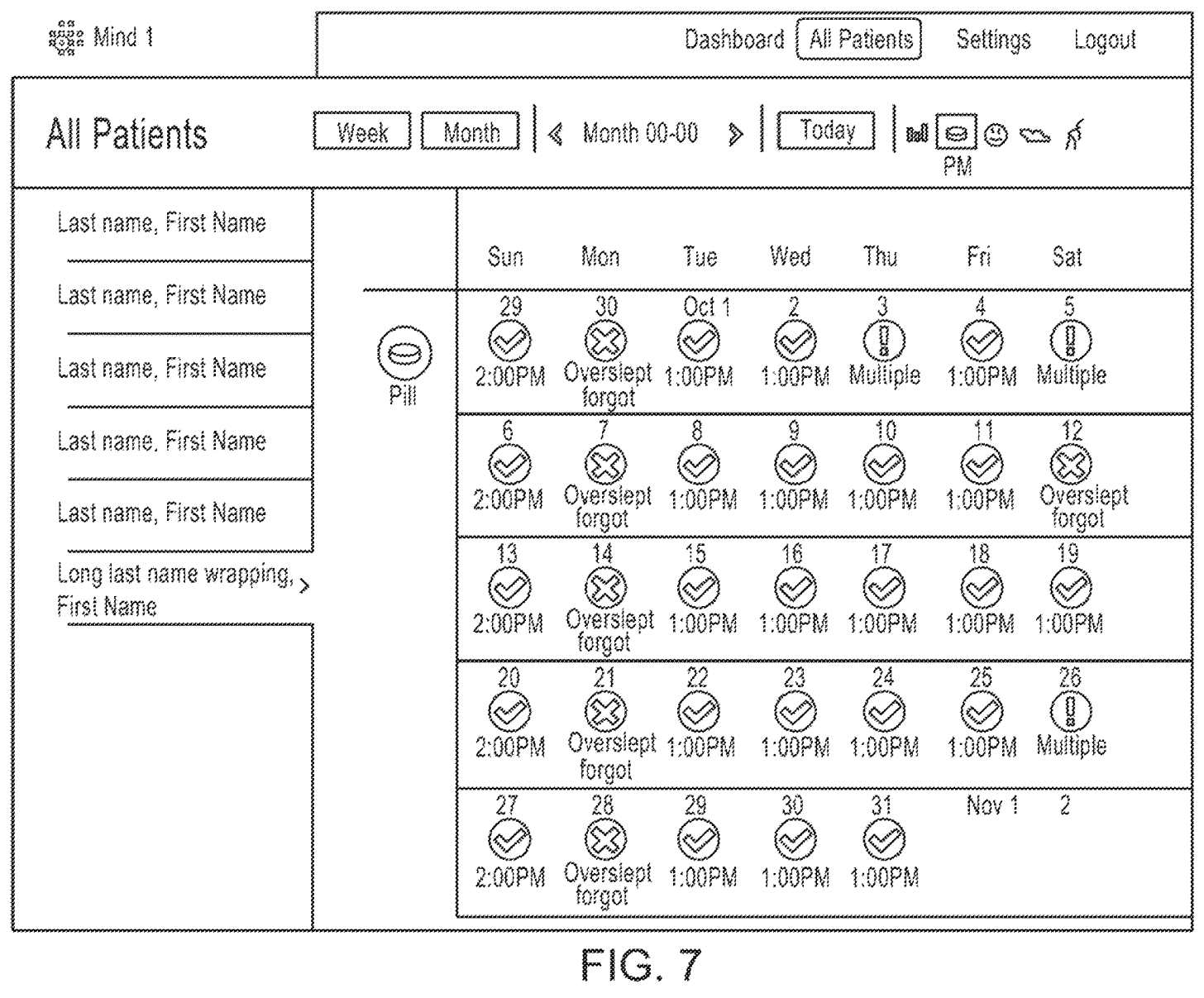

As described earlier, the memory 124 and/or the database 140 can store information associated with noncompliance (e.g., the response from the primary set of responses, the response from the modified primary set of responses, and/or the response from the secondary set of responses), as well as information associated with compliance (e.g., an indication of an ingestion event detected by the sensor 110), patient information, and/or the like. The stored information, whether stored on the compute device 100, the server 120, or elsewhere, can be accessible by the user, and/or another entity such as a caregiver of the user, a healthcare provider of the user, a manufacturer of the substance/medication, a distributor of the substance/medication, a pharmacy, and/or the like. FIG. 7 illustrates an exemplary interface for presenting noncompliance/compliance information to a healthcare provider monitoring compliance of multiple patients. For each patient, the interface of FIG. 7 illustrates a monthly view of compliance for a user, with check marks indicating compliance, cross marks indicating noncompliance, and exclamation marks indicating delayed compliance (e.g., the patient indicates that he took the dose after the predetermined time period). Similar interfaces as illustrated in FIG. 7 can be provided to other entities discussed herein, such as caregivers and pharmacists.

While described herein with reference to ingestible event markers for simplicity, it is understood that in some embodiments, other ingestion event detection approaches can be used such as, but not limited to, popping of a blister pack, opening of a container, pouring from a container, indication of ingestion by a witness, self-reporting, and/or the like.

Aspects of the compliance/noncompliance information collected can be useful for research purposes, as well as for optimization of compliance programs such as Risk Evaluation and Mitigation Strategy (REMS) programs. Trends identified by the compliance/noncompliance information can be used to provide improved guidance and/or counseling related to specific medication.

In other embodiments, at least some of the modules shown and described with respect to FIG. 2 as being executed on compute device 100 can be stored and/or executed on a server (e.g., server 120 of FIG. 1). Similarly stated, in some embodiments, at least some of the functions performed by the modules of FIG. 2 can instead be performed on a server. For example, the analytics module 130 and/or the action module 132 can be executed on the server 120. In such an example, the compute device 100 can send a signal to the server 120 with information that can be used by the analytics module 130 and/or the action module 132 to perform their respective functions. Specifically, the analytics module on the server can identify at least one trend associated with compliance and/or noncompliance of the user with the therapeutic regimen. Similarly, the action module on the server can generate queries to be provided to the user and send such queries to the compute device 100. In other embodiments, any other suitable functions described as being performed on the compute device 100 and/or any data described as being stored on the compute device 100, can be performed on and/or stored at a server. Similarly, in yet other embodiments, any suitable functions described as being performed on the server 120 and/or any data described as being stored on the server 120, can be performed on and/or stored at a compute device of a user.

While the system for assessing non-adherence is shown and described above with respect to FIG. 1 as having a server 120, in other embodiments the system does not include a server. In such embodiments, for example, the compute device 100 does not send compliance and/or non-compliance information to a server. In some embodiments, for example, the compute device 100 can be a mobile device of a user such as a smart phone and/or watch. In such embodiments, an application executing on the mobile device can include at least a portion of the functionality and/or the modules described above with respect to compute device 100 (shown in FIG. 2).

In some embodiments, an apparatus includes a sensor module, an adherence module, a communication module and an analytics module. The sensor module is configured to monitor a sensor for a sensor signal indicative of ingestion of a substance by a user. The adherence module is configured to, in response to the sensor module not receiving an indication within a predetermined time period that the sensor received the sensor signal, generate a query indicative of noncompliance of the user with a therapeutic regimen associated with the substance. The query includes a set of responses. The communication module is configured to transmit the query to the user and receive, in response to the transmitting, an indication of a selection of a response from the set of responses. The analytics module is configured to identify at least one trend associated with compliance of the user with the therapeutic regimen based on at least one of the response from the set of responses, timing information associated with the response from the set of responses, timing information associated with historical data of compliance of the user with the therapeutic regimen, frequency information associated with the response from the set of responses, or frequency information associated with historical data of compliance of the user with the therapeutic regimen.

In some embodiments, the set of responses is a first set of responses and the adherence module is configured to, in response to receiving the selection of the response from the first set of responses from the communication module: (1) remove the response from the first set of responses to define a modified first set of responses; and (2) generate a modified query including the modified first set of responses. In some embodiments, the communication module is configured to transmit the modified query to the user and receive a selection of a response from the modified first set of responses different from the response from the first set or responses. When the response from the modified first set of responses indicates user intent to provide additional user input, the communication module is configured to transmit to the user a second set of responses associated with the response from the modified first set of responses.

In some embodiments, the apparatus includes an action module configured to perform one or more actions based on the response from the set of responses. In some embodiments, the action module is configured to identify a remedial communication associated with the response from the set of responses and the communication module is configured to transmit the remedial communication to the user.

In some embodiments, the communication module is configured to transmit information associated with the response from the set of responses to at least one of the user, a caregiver of the user, a healthcare provider of the user, or an entity associated with the substance. In some embodiments, the apparatus includes a database module configured to store in a database the response from the set of responses.

In some embodiments, the predetermined time period is a first predetermined time period and the adherence module is configured to generate an indication associated with detection of ingestion of the substance during a second predetermined time period. In some embodiments the apparatus further includes a database module configured to store in a database the response from the set of response and store the indication. The analytics module can be configured to retrieve the response from the set of responses and the indication from the database prior to the analytics module identifying the at least one trend. The analytics module can be configured to identify the at least one trend based at least in part on the response from the set of responses and the indication.

In some embodiments, a non-transitory processor-readable medium stores code representing instructions to be executed by a processor. The code includes code to cause the processor to monitor, for a predetermined time period, a sensor for a sensor signal indicative of ingestion of a substance by a user and in response to not receiving an indication within the predetermined time period that the sensor received the sensor signal, generate a query including a first set of responses. The code further includes code to transmit the query to the user upon expiration of the predetermined time period and receive, in response to the transmitting the query, a selection of a response from the set of responses indicative of a reason of noncompliance of the user with a therapeutic regimen associated with the substance. The code further includes code to identify, based on the response from the set of responses, a remedial communication associated with the therapeutic regimen and transmit the remedial communication to the user based on the response from the set of responses.

In some embodiments, the set of responses is a first set of responses. In some embodiments, the non-transitory processor-readable medium further includes code to cause the processor to, after receiving the selection of the response from the set of responses: (1) modify the first set of responses to remove the response from the first set of responses to define a modified first set of responses; (2) generate a modified query including the modified first set of responses; (3) transmit the modified query; (4) receive a selection of a response from the modified first set of responses different from the response from the first set of responses; and (5) when the response from the modified first set of responses indicates user intent to provide additional user input, transmit a second set of responses associated with the response from the modified first set of responses.

In some embodiments, the predetermined time period is a first predetermined time period. In some embodiments, the non-transitory processor-readable medium further includes code to cause the processor to: (1) store the response from the set or responses in a database; (2) when the sensor signal meets a criterion indicative of detection of ingestion of the substance during a second predetermined time period, generate an indication; (3) store the indication in the database; and (4) analyze at least one or more of the response from the set of responses or the stored indication to identify a trend.

In some embodiments, the predetermined time period is a first predetermined time period and the non-transitory processor-readable medium further includes code to cause the processor to transmit, during a second predetermined time period after the first predetermined time period, a reminder to the user to ingest the substance within the second predetermined time period.

In some embodiments, the non-transitory processor-readable medium further includes code to cause the processor to transmit information associated with the response from the set of responses to at least one of the user, a caregiver of the user, a healthcare provider of the user, or an entity associated with the substance In some embodiments, a method includes monitoring a sensor for a sensor signal indicative of ingestion of a substance by a user and in response to not receiving an indication within a predetermined time period that the sensor received the sensor signal, generating a query including a first set of responses. Each response from the first set of responses is associated with a different second set of responses. The method further includes transmitting the query to the user and receiving, in response to the transmitting, an indication of a selection of a response from the first set of responses. The method further includes identifying the second set of responses associated with the response from the first set of responses and transmitting, in response to receiving the response from the first set of responses, the second set of responses associated with the response from the first set of responses. The method further includes receiving, in response to transmitting the second set of responses associated with the response from the first set of responses, a selection of one or more responses from the second set of responses associated with the response from the first set of responses. The one or more responses from the second set of responses can provide an explanation as to why the sensor did not receive the sensor signal within the predetermined time period.

In some embodiments, the method further includes, after receiving the selection of the response from the first set or responses: (1) removing the response from the first set of responses to define a modified first set of responses; (2) generating a modified query including the modified first set of responses; (3) transmitting the modified query to the user; (4) receiving a selection of a response from the modified first set of responses different from the response from the first set of responses; and (4) when the response from the modified first set of responses indicates user intent to provide additional user input, transmitting to the user the second set of responses associated with the response from the modified first set of responses.

In some embodiments, the method further includes performing one or more actions based on at least one of the response from the first set of responses or the one or more responses from the second set of responses. In some embodiments, the method further includes identifying a remedial communication associated with at least one of the response from the first set of responses or the one or more responses from the second set of responses, and transmitting the remedial communication to the user.

In some embodiments, the method further includes transmitting, based on at least one of the response from the first set of responses or the one or more responses from the second set of responses, information associated with at least one of the response from the first set of responses or the one or more responses from the second set of responses to at least one of the user, a caregiver of the user, a healthcare provider of the user, or an entity associated with the substance. In some embodiments, the method further includes storing in a database at least one of the response from the first set of responses or the one or more responses from the second set of responses.

In some embodiments, the predetermined time period is a first predetermined time period and the sensor signal is a first sensor signal. In some embodiments, the method includes: (1) storing in a database at least one of the response from the first set of responses or the one or more responses from the second set of responses; (2) in response to receiving a second sensor signal indicative of detection of ingestion of the substance within a second predetermined time period, generating an indication; (3) storing the indication in the database; and (4) analyzing at least one or more of the stored response from the first set of responses, the stored one or more responses from the second set of responses, or the stored indication.

While various embodiments have been described herein, it should be understood that they have been presented by way of example, and not limitation. Where methods described above indicate certain events occurring in certain order, the ordering of certain events may be modified. Additionally, certain of the events may be performed concurrently in a parallel process when possible, as well as performed sequentially as described herein.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments have been described above, it should be understood that they have been presented by way of example, and not limitation. Where methods described above indicate certain events occurring in certain order, the ordering of certain events can be modified. Additionally, certain of the events may be performed concurrently in a parallel process when possible, as well as performed sequentially as described above.

What is claimed is:

1. A system, comprising:
an ingestible signal generator coupled to a medication and configured to generate a body-transmissible signal upon ingestion by a user;
a receiver configured to be disposed on the body of the user during use, the receiver including a sensor configured to detect the body-transmissible signal, the receiver further configured to generate and wirelessly transmit a sensor signal based on the body-transmissible signal; and
a user device associated with the user, the user device including a processor and a memory, the processor configured to:
wirelessly monitor the sensor for the sensor signal;
in response to the processor not receiving the sensor signal within a predetermined time period, generate a notification including a first set of responses;
send a signal to present the notification to the user;
receive, in response to the presenting, a response to the notification from the user, the response to the notification being a selected response from the first set of responses, the first set of responses including the selected response and remaining responses, each response from the first set of responses including an indication as to why the processor did not receive the sensor signal within the predetermined time period;
identify at least one trend associated with the sensor signal and the medication based on the response to the notification and a history associated with the medication;
perform one or more actions based on the response to the notification and the at least one trend;
remove, in response to receiving the selected response from the first set of responses, the selected response from the first set of responses to define a modified first set of responses, the modified first set of responses including at least some of the remaining responses from the first set of responses;
generate a modified query including the modified first set of responses;
send a signal to present the modified query;
receive a selection of a response from the modified first set of responses different from the response from the first set of responses; and
when the response from the modified first set of responses includes an indication of additional user input, send a signal to present a second set of responses associated with the response from the modified first set of responses.

2. The system of claim 1, wherein the processor of the user device is further configured to identify a communication associated with the response to the notification, the processor configured to send a signal to present the communication.

3. An apparatus, comprising:
an antenna;
a memory; and
a processor operatively coupled to the antenna and the memory, the processor configured to wirelessly monitor, via the antenna, a sensor of an ingestible signal generator for a sensor signal indicative of ingestion of a substance by a user, the sensor configured to transmit the sensor signal upon detection of a body-transmissible signal generated upon ingestion, by the user, of the ingestible signal generator coupled to a medication, the processor configured to:
in response to the sensor not receiving the sensor signal within a predetermined time period, generate a notification including a first set of responses;
send a signal to present the notification;
receive, in response to the presenting, a response to the notification from the user, the response to the notification being a selected response from the first set of responses, the first set of responses including the selected response and remaining responses, each response from the first set of responses including an indication as to why the processor did not receive the sensor signal within the predetermined time period;
identify at least one trend associated with the sensor signal based on the response to the notification;
perform one or more actions based on the response to the notification;
remove, in response to receiving the selected response from the first set of responses, the selected response from the first set of responses to define a modified first set of responses, the modified first set of responses including at least some of the remaining responses from the first set of responses;
generate a modified query including the modified first set of responses;
send a signal to present the modified query;

receive a selection of a response from the modified first set of responses different from the selected response from the first set of responses; and when the response from the modified first set of responses includes an indication of additional user input, send a signal to present a second set of responses associated with the response from the modified first set of responses.

4. An apparatus, comprising:

a memory; and a processor operatively coupled to the memory, the processor configured to:

monitor a sensor of an ingestible signal generator for a sensor signal indicative of ingestion of a substance by a user, the sensor configured to transmit the sensor signal upon detection of a body-transmissible signal generated upon ingestion, by the user, of the ingestible signal generator coupled to a medication;

in response to the processor not receiving the sensor signal within a predetermined time period, generate a query including a first set of responses;

send a signal to present the query;

receive from the user, in response to presenting the query, an indication of a selected response from the first set of responses, the first set of responses including the selected response and remaining responses, each response from the first set of responses including an indication as to why the processor did not receive the sensor signal within the predetermined time period;

identify at least one trend associated with compliance of the user with a therapeutic regimen based on at least one of the selected response from the set of responses, timing information associated with the selected response from the set of responses, timing information associated with historical data of compliance of the user with the therapeutic regimen, frequency information associated with the selected response from the set of responses, or frequency information associated with historical data of compliance of the user with the therapeutic regimen;

perform one or more actions based on the selected response from the first set of responses;

remove, in response to receiving the selected response from the first set of responses, the selected response from the first set of responses to define a modified first set of responses, the modified first set of responses including at least some of the remaining responses from the first set of responses;

generate a modified query including the modified first set of responses;

send a signal to present the modified query;

receive a selection of a response from the modified first set of responses different from the selected response from the first set of responses; and when the response from the modified first set of responses includes an indication of additional user input, send a signal to present a second set of responses associated with the response from the modified first set of responses.

5. The apparatus of claim 4, the processor further configured to identify a communication associated with the selected response from the first set of responses, the processor configured to send a signal to present the communication.

6. The apparatus of claim 4, the processor further configured to store, in a database, the selected response from the first set of responses.

7. The apparatus of claim 4, wherein the predetermined time period is a first predetermined time period, the processor is configured to generate an indication associated with detection of ingestion of the substance during a second predetermined time period, the processor further configured to:

store, in a database, the selected response from the first set of responses;

store the indication associated with detection of ingestion of the substance during the second predetermined time period; and retrieve the response from the first set of responses and the indication associated with detection of ingestion of the substance during the second predetermined time period from the database prior to the processor identifying the at least one trend, the processor configured to identify the at least one trend based at least in part on the selected response from the first set of responses and the indication associated with detection of ingestion of the substance during the second predetermined time period.

8. A non-transitory processor-readable medium storing code representing instructions to be executed by a processor, the code comprising code to cause the processor to:

monitor, for a predetermined time period, a sensor of an ingestible signal generator for a sensor signal indicative of ingestion of a substance by a user, the sensor configured to transmit the sensor signal upon detection of a body-transmissible signal generated upon ingestion, by the user, of the ingestible signal generator coupled to a medication;

in response to the sensor not receiving the sensor signal within the predetermined time period, generate a query including a first set of responses;

send a signal to present the query upon expiration of the predetermined time period;

receive from the user, in response to the presenting, a selection of a selected response from the first set of responses, the first set of responses including the selected response and remaining responses, each response from the first set of responses including an indication as to why the processor did not receive the sensor signal within the predetermined time period;

identify, based on the selected response from the first set of responses, a remedial communication associated with a therapeutic regimen of the substance;

send a signal to present the remedial communication based on the selected response from the first set of responses;

modify the first set of responses to remove the selected response from the first set of responses to define a modified first set of responses, the modified first set of responses including at least some of the remaining responses from the first set of responses;

generate a modified query including the modified first set of responses;

send a signal to present the modified query;

receive a selection of a response from the modified first set of responses different from the selected response from the first set of responses; and when the response from the modified first set of responses includes an indication of additional user input, send a signal to present a second set of responses associated with the response from the modified first set of responses.

9. The non-transitory processor-readable medium of claim 8, wherein the predetermined time period is a first predetermined time period, the code further comprising code to cause the processor to:
store the selected response from the first set of responses in a database;
when the sensor signal meets a criterion indicative of detection of ingestion of the substance during a second predetermined time period, generate an indication;
store the indication in the database; and
analyze at least one or more of the selected response from the first set of responses or the stored indication to identify a trend.

10. The non-transitory processor-readable medium of claim 8, wherein the predetermined time period is a first predetermined time period, the code further comprising code to cause the processor to:
send a signal to present, during a second predetermined time period after the first predetermined time period, a reminder to ingest the substance within the second predetermined time period.

11. A method, comprising:
monitoring a sensor of an ingestible signal generator for a sensor signal indicative of ingestion of a substance by a user, the sensor configured to transmit the sensor signal upon detection of a body-transmissible signal generated upon ingestion, by the user, of the ingestible signal generator coupled to a medication;
in response to not receiving, at a processor of a computing device, the sensor signal within a predetermined time period, generating a query including a first set of responses, each response from the first set of responses associated with a different second set of responses;
sending a signal to present the query;
receiving from the user, in response to the presenting, an indication of a selected response from the first set of responses, the first set of responses including the selected response and remaining responses, each response from the first set of responses including an indication as to why the processor did not receive the sensor signal within the predetermined time period;
after receiving the selected response from the first set of responses, removing the selected response from the first set of responses to define a modified first set of responses, the modified first set of responses including at least some of the remaining responses from the first set of responses;
generating a modified query including the modified first set of responses;
sending a signal to present the modified query;
receiving a selection of a response from the modified first set of responses different from the selected response from the first set of responses;
when the response from the modified first set of responses indicates user intent to provide additional user input, sending a signal to present a second set of responses associated with the response from the modified first set of responses; and
receiving from the user, in response to presenting the second set of responses associated with the response from the modified first set of responses, a selection of one or more responses from the second set of responses associated with the response from the modified first set of responses, the one or more responses from the second set of responses including an indication as to why the sensor did not receive the sensor signal within the predetermined time period; and performing one or more actions based on at least one of the selected response from the first set of responses or the one or more responses from the second set of responses.

12. The method of claim 11, further comprising:
identifying a communication associated with at least one of the selected response from the first set of responses or the one or more responses from the second set of responses; and
sending a signal to present the communication.

13. The method of claim 11, further comprising storing in a database at least one of the selected response from the first set of responses or the one or more responses from the second set of responses.

14. The method of claim 11, wherein the predetermined time period is a first predetermined time period and the sensor signal is a first sensor signal, the method further comprising:
storing in a database at least one of the selected response from the first set of responses or the one or more responses from the second set of responses;
in response to receiving a second sensor signal indicative of detection of ingestion of the substance within a second predetermined time period, generating an indication;
storing the indication generated in response to receiving the second sensor signal indicative of detection of ingestion of the substance within the second predetermined time period in the database; and
analyzing at least one or more of the stored selected response from the first set of responses, the stored one or more responses from the second set of responses, or the stored indication.

15. A system, comprising:
an ingestible signal generator coupled to a medication and configured to generate a body-transmissible signal upon ingestion by a user;
a receiver configured to be disposed on the body of the user during use, the receiver including a sensor configured to detect the body-transmissible signal, the receiver further configured to generate and wirelessly transmit a sensor signal based on the body-transmissible signal; and
a user device associated with the user, the user device including a processor and a memory, the processor configured to:
wirelessly monitor the sensor for the sensor signal;
in response to the processor not receiving the sensor signal within a predetermined time period, generate a notification including a first set of responses;
send a signal to present the notification to the user;
receive, in response to the presenting, a response to the notification from the user, the response to the notification being a selected response from the first set of responses, the first set of responses including the selected response and remaining responses, each response from the first set of responses including an indication as to why the processor did not receive the sensor signal within the predetermined time period;
remove, in response to receiving the selected response from the first set of responses, the selected response from the first set of responses to define a modified first set of responses, the modified first set of responses including at least some of the remaining responses from the first set of responses;
generate a modified query including the modified first set of responses;

send a signal to present the modified query;

receive a selection of a response from the modified first set of responses different from the selected response from the first set of responses;

when the response from the modified first set of responses includes an indication of additional user input, send a signal to present a second set of responses associated with the response from the modified first set of responses;

identify at least one non-compliance trend associated with the sensor signal and the medication based on the selected response and a history associated with the medication, the non-compliance trend associated with the user; and perform one or more actions to assist in remedying the non-compliance trend based on the response from the modified first set of responses and the at least one trend, wherein the one or more actions includes at least one of:

providing, to a non-user entity, literature on how to counsel the user based on the response to the notification from the user;

searching a network including at least one of an internet or one or more trusted sources to identify search results including at least one of a remedial communication or the literature;

populating at least one of the memory or one or more databases with the search results; or notifying an entity associated with the user about the response to the notification from the user and/or the at least one non-compliance trend.

16. The system of claim 1, wherein the first set of responses includes a response that the medication was ingested within the predetermined time period and the sensor signal was not received in error.

17. The system of claim 1, wherein the first set of responses includes a response that the medication was ingested by the user after the predetermined time period.

18. The apparatus of claim 3, wherein the first set of responses includes a response that the medication was ingested within the predetermined time period and the sensor signal was not received in error.

19. The apparatus of claim 3, wherein the first set of responses includes a response that the medication was ingested by the user after the predetermined time period.

20. The apparatus of claim 4, wherein the first set of responses includes a response that the medication was ingested within the predetermined time period and the sensor signal was not received in error.

21. The apparatus of claim 4, wherein the first set of responses includes a response that the medication was ingested by the user after the predetermined time period.

22. The non-transitory processor-readable medium of claim 8, wherein the first set of responses includes a response that the medication was ingested within the predetermined time period and the sensor signal was not received in error.

23. The non-transitory processor-readable medium of claim 8, wherein the first set of responses includes a response that the medication was ingested by the user after the predetermined time period.

24. The method of claim 11, wherein the first set of responses includes a response that the medication was ingested within the predetermined time period and the sensor signal was not received in error.

25. The method of claim 11, wherein the first set of responses includes a response that the medication was ingested by the user after the predetermined time period.

26. The system of claim 15, wherein the first set of responses includes a response that the medication was ingested within the predetermined time period and the sensor signal was not received in error.

27. The system of claim 15, wherein the first set of responses includes a response that the medication was ingested by the user after the predetermined time period.

* * * * *